United States Patent [19]

Ng

[11] Patent Number: 4,995,386

[45] Date of Patent: Feb. 26, 1991

[54] NEONSTAL MUCUS EXTRACTOR

[76] Inventor: Raymond C. Ng, 1737 Oak Grove Ave., San Marino, Calif. 91108

[21] Appl. No.: 358,566

[22] Filed: May 30, 1989

Related U.S. Application Data

[63] Continuation-in-part of Ser. No. 273,022, Nov. 18, 1988, Pat. No. 4,947,841.

[51] Int. Cl.$^5$ .............................................. A62B 7/00
[52] U.S. Cl. ............................. 128/205.19; 128/760; 604/319
[58] Field of Search ............... 128/207.14, 207.15, 128/200.26, 10, 760; 604/19, 27, 35, 76, 319; 215/1 C, DIG. 3

[56] References Cited

U.S. PATENT DOCUMENTS

| Re. 29,321 | 7/1977 | Holbrook | 604/319 |
|---|---|---|---|
| 1,137,388 | 4/1915 | Earp-Thomas | 215/DIG. 3 |
| 2,700,973 | 2/1955 | Ju | 604/76 |
| 4,207,894 | 6/1980 | Klibansky | 604/319 |
| 4,321,921 | 3/1982 | Laszczower | 604/35 |
| 4,460,361 | 7/1984 | Nichols | 604/319 |
| 4,787,894 | 11/1988 | Turnbull | 604/319 |
| 4,791,914 | 12/1988 | May | 128/10 |
| 4,799,925 | 1/1989 | Rosenblatt | 215/DIG. 3 |
| 4,813,931 | 3/1989 | Hauze | 128/760 |

Primary Examiner—David A. Wiecking
Assistant Examiner—Aaron J. Lewis
Attorney, Agent, or Firm—William W. Haefliger

[57] ABSTRACT

A suctioning device is provided for use in removal of fluid mucus from the trachea and nostrils of a newborn infant, to prevent aspiration of such fluid into the infant's lungs before first breath; the device includes a vertically, longitudinally, upright container having a bottom wall with an opening therein to pass mucus into the container via a tubular catheter, and a top cap with an opening therein to pass suction air from the container interior toward a suction mouthpiece; a baffle or baffles in the container to intercept upward flow of mucus toward the top cap; a duct in the container to receive flow of mucus via the opening in the bottom wall, the duct having an outlet end located to eject mucus to fall in a generally downward direction in the container, below the baffle; and a filter or filter above the duct to filter air being sucked from the container interior toward the mouthpiece via the top cap opening.

The filter and one part of the baffle are typically carried by the top cap for endwise insertion downwardly into the container upper extent, the bottom wall is typically defined by a bottom cap received in the container, and the duct and a second part of the baffle are typically carried by the bottom cap for endwise insertion upwardly into lower end extent of the container.

21 Claims, 2 Drawing Sheets

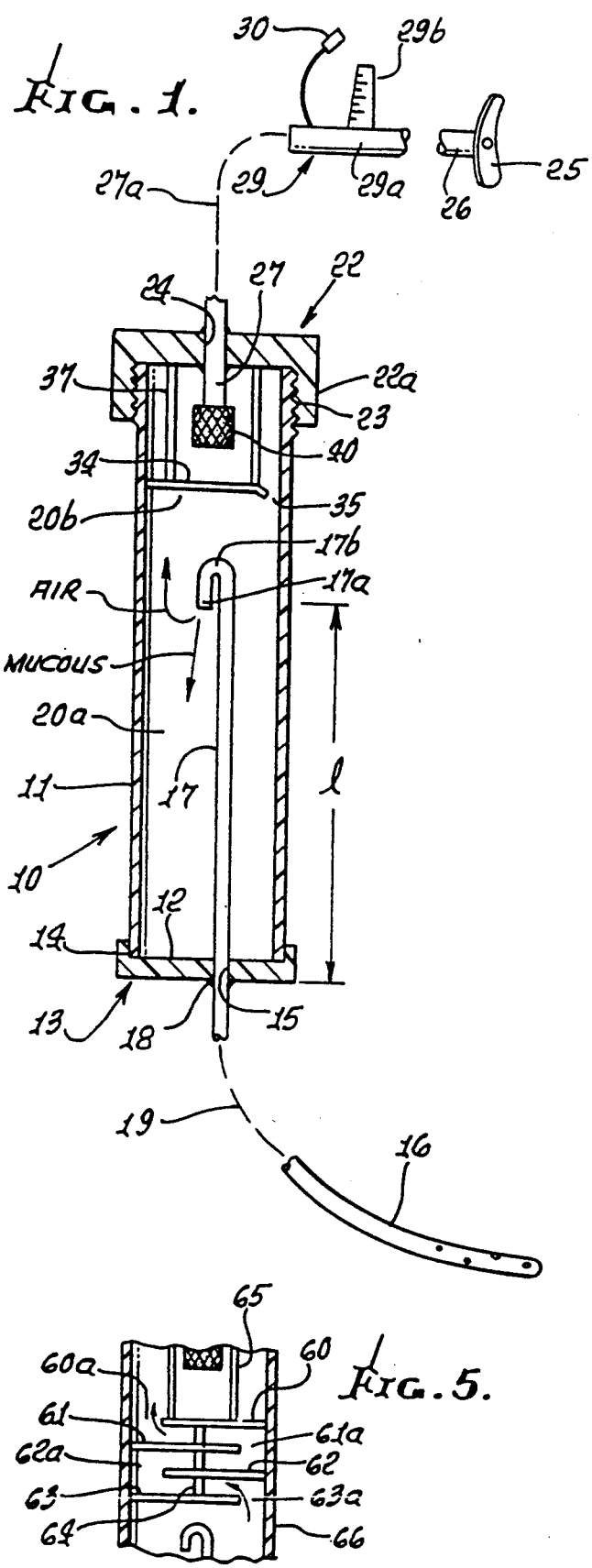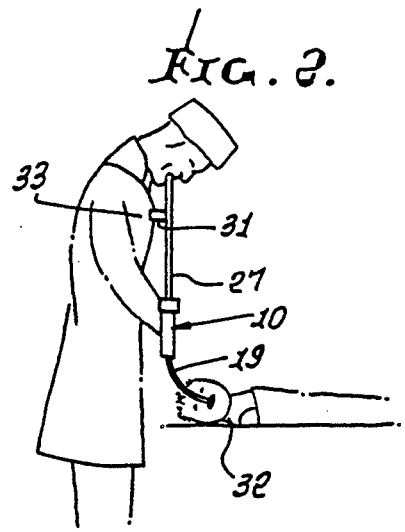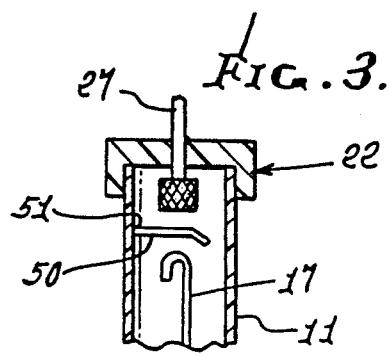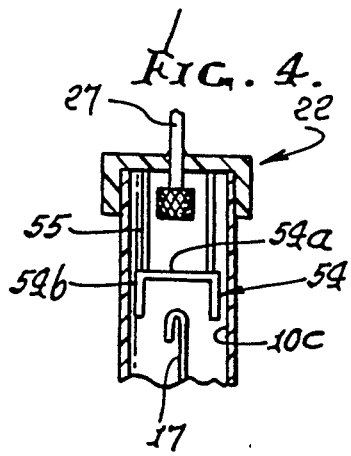

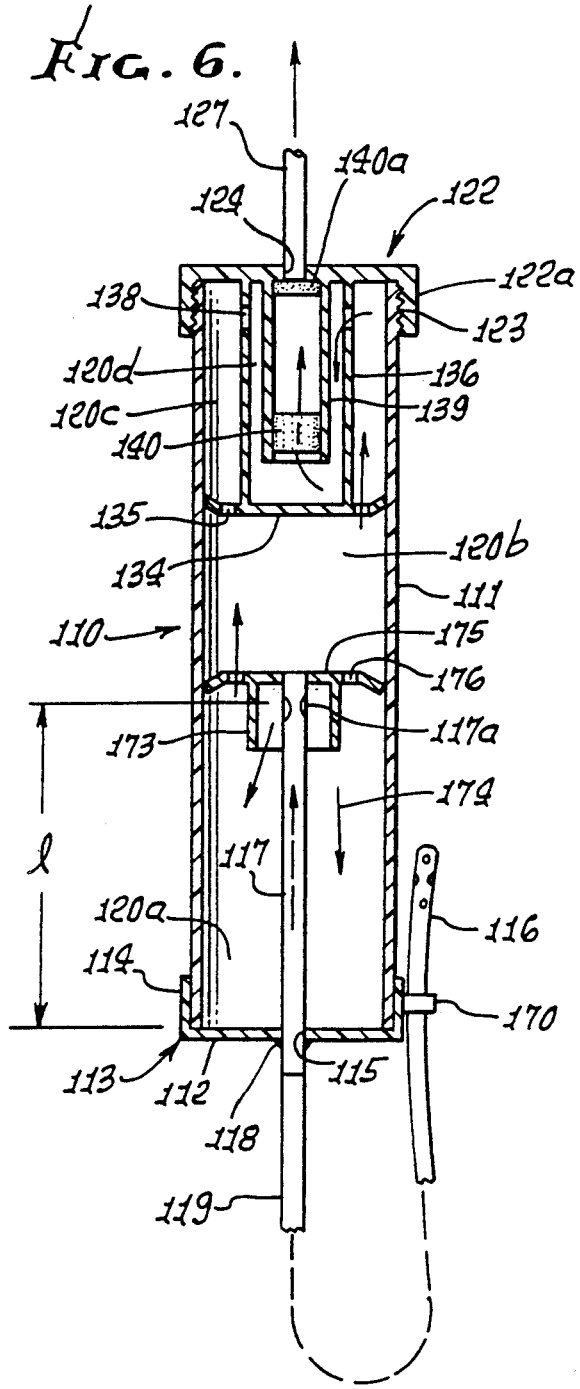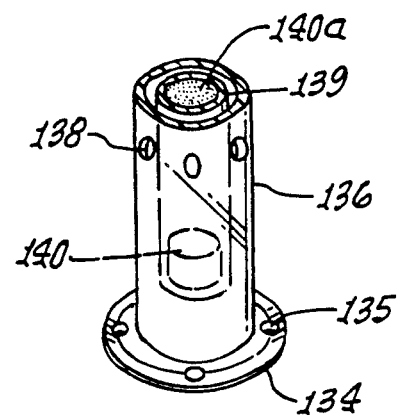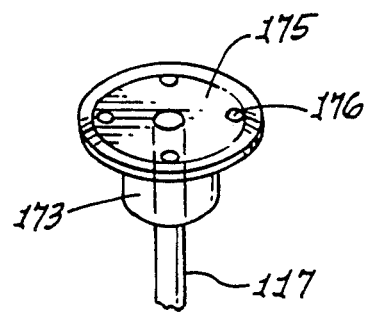

NEONSTAL MUCUS EXTRACTOR

BACKGROUND OF THE INVENTION

This application is a continuation-in-part of Ser. No. 273,022 filed Nov. 18, 1988 now U.S. Pat. No. 4,947,841. The invention relates generally to a simple oral and mechanical suctioning of mucus and debris from a newborn infant's mouth and nostrils at the time of birth to prevent aspiration of such fluids into the lungs before the first breath.

Suctioning devices currently in use consist of a container with both an oral catheter (to the infant's mouth) and the suction tubing (to the operator for oral suctioning) attached to one end of the container in close proximity to each other, often resulting in the incidental contact on the operator of fluids and debris from the infant. Such fluids sometimes can contain infectious agents (i.e., Hepatitis, AIDS virus, etc.).

There is great need for improved suctioning means that eliminates the above problem, and which also makes the suctioning device easier to employ, and to support during use.

SUMMARY OF THE INVENTION

It is a major object of the invention to provide an improved device that allows efficient suctioning of the newborn infant's mouth and nostrils at the time of birth, and at the same time eliminates the possibility of suctioning such fluids into the operator's mouth, for safety reasons.

This is made possible in accordance with the invention by separating the suction tubing and the oral catheter to connect to the two opposite ends of the mucus container and also by interrupting the air flow through the container during suctioning by incorporating a deflecting baffle means. The air flow is typically further diverted away from the suctioning tubing by a tube with a bent open end inside the container, and connected to the oral catheter.

Also, the invention allows a more efficient way to suction the infant's mouth as a full view of the infant's oral cavity is possible without blockage by the device itself. This objective is realized by provision for support of the device, as will appear.

Basically, the invention is embodied in a device that comprises:

(a) a vertically, longitudinally, upright container, including bottom and top walls, a lower opening into the container to pass mucus into the container via a tubular catheter, and a upper opening in the container to pass suction air from the container interior toward a suctioning mouthpiece, (b) first and second means received into the container and at lengthwise spaced elevations therein, for preventing aspiration of mucus from the tube interior to pass upwardly via said top opening, (c) and flexible means supporting the container to hang vertically.

As will appear, third means separating air and mucus may also be provided in the container, and the first, second and third means may typically include, respectively, in sequence, a duct to direct flow of fluid downwardly in the container, a baffle extending sidewardly in the container to intercept upwardly flow of mucus, and a filter above the baffle.

Further objects include the provision of a duct that extends generally vertically in the container toward the baffle means, and has a downward bent outlet end portion or a side opening; the provision of baffle means that extend generally laterally in the container in association with the duct to form an air passing opening or openings; the provision of baffle means supported by a removable top cap, whereby the baffle means and filter may both be removed as a unit, with the top cap, from the container; the provision of various unusually advantageous baffle configurations, as will appear to establish countercurrent or flow deflecting air flow pattern for assuring removal of mucus from the reversing air stream; and provision for full viewing of the container and duct contents.

These and other objects and advantages of the invention, as well as the details of illustrative embodiments, will be more fully understood from the following specification and drawings, in which:

DRAWING DESCRIPTION

FIG. 1 is a vertical elevation in section showing one form of the device of the invention;

FIG. 2 is a view showing suspension of the device from the user's clothing, during use of the device;

FIGS. 3, 4, and 5 are fragmentary sections showing modified baffle arrangements;

FIG. 6 is a view like FIG. 1, showing a modified device;

FIG. 7 is a perspective view of an upper air flow deflecting and filter assembly; an FIG. 8 is a perspective view of a lower air flow deflecting and inlet duct assembly.

DETAILED DESCRIPTION

In FIG. 1, a tubular container 10 is longitudinally, vertically oriented. It has a transparent side wall 11 via which the extent of mucus filling into the container can be viewed. The container may consist for example of synthetic resin, i.e., plastic material.

The container has a bottom wall 12, as may be formed by a bottom cap 13 attached to the lowermost extent of the container, as at 14. A suitable adhesive may provide the attachment. The bottom wall has an opening 15 therein, to pass mucus into the container as from a tubular catheter 16. The latter is typically inserted into the infant's trachea, at birth, to remove mucus prior to first breath.

A duct 17 extends upright within the container to receive flow of air entrained mucus entering the container via opening 15, and for this purpose, the duct may pass through the opening and be attached to the bottom wall, as by adhesive at 18. The duct connects with the catheter via a flexible duct 19. The duct 17 within the container is substantially rigid to stand upright. The duct may typically have an outlet opening 17a directed downwardly, and for this purpose the uppermost extent 17b of the duct may be bent or curved reversely, to open at 17a, generally downwardly. Entering air then separates from entrained mucus in the lower interior of the container. Thus, mucus leaving the tract during suction into the container is directed toward the lower interior 20a of the container, i.e., away from the upper interior 20b to which suction is applied. Note that bent portion 17b is well above the bottom wall 12 to provide mucus fill space of a length "1", which is typically more than half the overall length of the tubular container. Outlet 17a should remain above the mucus filling the container, the level of which may be viewed via the transparent wall of the container. Duct 17 typically consists of transparent plastic, i.e., has a transparent side wall.

A top cap 22 is provided to close the uppermost extent of the container. It advantageously has a skirt 22a removably thread connected to the container at 23, whereby the cap may be quickly removed, if necessary, as for pour-out removal of mucus from the container. The two caps 13 and 22 may also consist of plastic material.

The top cap has an opening 24 thereinto pass suction air from the container interior, as toward a mouthpiece 25 connected in series with flexible tubing 26. A flexible duct 27 is typically connected with the mouthpiece and extends freely at 27a to support the container to hang vertically Duct 27 also may extend into the container upper interior via opening 24, and the duct may be attached to the top cap as by suitable adhesive, or other means. An aspiration control 29 may be connected in series with the duct 27 whereby variable aspiration control is obtained. Note that 29 includes a tubular main leg 29a in series with duct 27, and a tubular side leg 29b branching from 29a. A plug 30 may be fitted into the end of leg 29b to close it; otherwise, variable finger closure of the open end of leg 29b allows variable control of aspiration. FIG. 2 shows a clip 31 on the duct 27 to attach to the user's clothing 33, and thereby suspend the device to hang freely vertically, during aspiration of the infant, seen at 32.

The baffle means is provided in the container to intercept upward flow of mucus in the air being removed by suction from the container interior via duct or tube 27. The baffle 34 extends laterally in FIG. 1 to block the direct upward flow of mucus while passing suction air. See narrow gap 35 at the edge of the baffle, and located between the edge and a small extent (less than 60° about the tube axis) of the container inner wall. The baffle is suspended by hanger 37 from the top cap 22. A mucus filter 40 is located above the baffle, at the lower end of duct 27, to remove any remaining mucus from the leaving air stream. Thus, when the top cap is removed, mucus may be poured from the container, the baffle and filter being attached to the top cap. This also facilitates direct inspection of the baffle and filter.

In FIG. 3, the baffle 50 is like 34, but it is attached to the container wall at 51, about that wall circumference, except for the gap area.

In FIG. 4, the baffle 54 has a top lateral wall 54a suspended at 55 from the top cap 22 so that the periphery of wall 54a is narrowly spaced from the container inner wall 10c. Also, it has an annular skirt 54b that depends to form a narrow gap 56 with wall 10c. That gap passes suction air upwardly, while the baffle top wall 54a blocks upward flow of mucus.

In FIG. 5, a vertical succession of lateral baffles or plates 60-63 is connected together at 64, and the top baffle suspended at 65 from the top cap, as before. Staggered air passing gaps are provided by baffle edges with the container wall 66, as at 60a-63a. This provides a tortuous air path which effectively blocks upward flow of mucus to the filter.

In FIG. 6, a tubular container 110 is longitudinally, vertically oriented. It has a transparent side wall 111 via which the extent of mucus filling into the container can be viewed. The container may consist for example of synthetic resin, i.e., plastic material.

The container has a bottom wall 112, as may be formed by a bottom cap or lower end cap 113 attached to the lowermost extent of the container, via the cap skirt, as at 114. A suitable adhesive may provide the attachment, or the skirt may be screw thread attached to the container. The bottom wall has an opening 115 therein, to pass mucus into the container as from a flexible, tubular duct 119 terminating at a catheter 116. The latter is typically inserted into the infant's trachea, at birth, to remove mucus prior to first breath. A clip-type hanger or holder 170 on the lower cap provides a means to store the catheter when not in use.

A duct 117 extends upright within the container to receive flow of air entrained mucus entering the container via opening 115, and for this purpose, the duct may pass through the opening and be attached to the bottom wall, as by adhesive, at 118. The duct 117 connects with the catheter via flexible duct 119, and within the container the duct 117 is substantially rigid to stand upright. The duct upper end extent has a side outlet opening 117a directed sidewardly, for mucus to impinge on upright tubular baffle 173 that extends about the duct upper extent and is spaced therefrom. Entering air then separates from entrained mucus, which falls at 174 into the lower interior of the container. Thus, mucus leaving the tract during suction into the container is directed toward the lower interior 120a of the container, i.e., away from the upper interior 120b to which suction is applied.

Another baffle 175 extends laterally horizontally into close proximity with the side wall 111 and is typically attached to the upper end of the duct 117 to be insertible into the container when cap 113 is attached to the container. Baffle 175 carries baffle 173, and forms an opening or openings 176 to pass air upwardly from region 120a. See FIG. 8.

Note that side outlet 117a is well above the bottom wall 112 to provide mucus fill space of a length "1", which is typically about half or more than half the overall length of the tubular container. Outlet 117a should remain above the mucus filling the container, the level of which may be viewed via the transparent wall of the container. Duct 117 typically consists of transparent plastic, i.e., has a transparent side wall.

A top cap 122 is provided to close the uppermost extent of the container. It advantageously has a skirt 122a removably thread connected to the container at 123, whereby the cap may be quickly removed, if necessary, as for pour-out removal of mucus from the container. The two caps 113 and 122 may also consist of plastic material.

The top cap has an opening 124 therein to pass suction air from the container interior, as toward a mouthpiece 25 (see FIG. 1) connected in series with flexible tubing 127. Flexible duct 127 is typically connected with the mouthpiece and extends freely to support the container to hang vertically, as described above. Duct 127 also may extend into the container upper interior via opening 124, and the duct may be attached to the top cap as by suitable adhesive, or other means. An aspiration control 29 may be connected in series with the duct 127 whereby variable aspiration control is obtained, as described above. Note that 29 includes a tubular main leg 29a in series with corresponding duct 127, and a tubular side leg 29b branching from 29a. A plug 30 may be fitted into the end of leg 29b to close it; otherwise, variable finger closure of the open end of leg 29b allows variable control of aspiration. FIG. 2 shows a clip 31 on the corresponding duct 27 to attach to the user's clothing 33, and thereby suspend the device to hang freely vertically, during aspiration of the infant, seen at 32.

Additional baffle means is provided in the container to intercept upward flow of mucus in the air being removed by suction from the container interior via duct or tube 127. Thus baffle 134 extends laterally in FIG. 6 to block the direct upward flow of remnant mucus, while passing suction air. See small openings 135 in the baffle, outwardly of a tube 136 that supports baffle 134 at the lower end of the tube, the tube upper end attached to the top cap, as shown. Thus, the baffle 134 and tube 136 are insertible as a unit downwardly into the container when the top cap is assembled to the container.

Suction air passes upwardly in region 120c above baffle 134 and outwardly of tube 136, then through side openings 138 in the tube upper extent, and then downwardly in region 120d between the tube and a second vertical tube 139 suspended from the top cap. A mucus filter 140 is located above the baffle 134, at and within the lower end of tube 139, to remove any remaining mucus from the leaving air stream, and another filter 140a may be located in the upper end extent of the tube. Thus, when the top cap is removed, mucus may be poured from the container, the baffle and filters 134, tubes 136 and 139, being carried by the top cap. This also facilitates direct inspection of the baffle and filter. The filters may comprise microfilters.

The construction, as referred to in FIGS. 6–8, enables very simple and rapid assembly of the sub-components into the cylindrical container 110, since the two end caps carry all of the sub-component structure. The latter is easily mounted on the caps, before their insertion into the container 113.

I claim:

1. In a suctioning device for use in removal of fluid mucus from the trachea and nostrils of a newborn infant, to prevent aspiration of such fluid into the infant's lungs before first breath, the combination comprising:
   (a) a vertically, longitudinally, upright container having a bottom wall with an opening therein to pass mucus into the container via a tubular catheter, and a top cap with an opening therein to pass suction air from the container interior toward a suction mouthpiece,
   (b) a baffle means in the container to intercept upward flow of mucus toward the top cap,
   (c) a duct in the container to receive flow of mucus via the opening in the bottom wall, the duct having an outlet end located to eject mucus to fall in a generally downward direction in the container,
   (d) and a filter above the baffle, to filter air being sucked from the container interior toward the mouthpiece via the top cap opening and wherein the filter and one part of the baffle means are carried by the top cap for endwise insertion downwardly into the upper extent of the container, which is tubular, and wherein there is a bottom cap on the container and which defines said bottom wall, the duct and another part of the baffle means are carried by the bottom cap for endwise insertion upwardly into the lower extent of the container.

2. The combination of claim 1 wherein the duct extends generally vertically in the container toward the baffle means, and has a downwardly bent outlet end portion.

3. The combination of claim 1 wherein the container has a transparent upright wall for viewing of the duct and baffle means.

4. The combination of claim 1 wherein the baffle means extends generally laterally in the container to form with the side wall in air passing opening or openings adjacent said side wall.

5. The combination of claim 3 wherein the baffle means is attached to the container side wall.

6. The combination of claim 4 wherein the baffle means is attached to the container side wall.

7. The combination of claim 1 wherein the baffle means extends generally laterally in the container and is suspended by the top cap.

8. The combination of claim 1 including suction tubing attached to the top cap, and suspending the container to hang vertically.

9. The combination of claim 8 wherein the air filter is located proximate the top cap and in alignment with the suction tubing.

10. The combination of claim 1 wherein the baffle means includes a series of baffles forming with the container a tortuous air flow path.

11. The combination of claim 1 wherein the baffle means includes a lateral wall and an annular skirt spaced narrowly from an inner wall defined by the container.

12. In a suctioning device for us in removal of fluid mucus from the trachea and nostrils of a newborn infant, to prevent aspiration of such fluid into the infant's lungs before first breath, the combination comprising:
   (a) a vertically, longitudinally upright tubular container having a lower end cap with an opening therein to pass mucus into the container via a tubular catheter, and a top cap with an opening therein to pass suction air from the container interior toward a suction mouthpiece,
   (b) a duct in the container and associated with the lower end cap to receive flow of mucus via said opening in the lower end cap, the duct having a outlet end located to eject mucus to fall in a generally downward direction in the container,
   (c) first and second baffle means in the container to intercept upward flow of mucus toward the top cap, and a filter in series with the baffle means to filter air being sucked from the container interior toward the mouthpiece via the top cap opening, said filter being associated with the top cap,
   (d) the first baffle means carried by the top cap and the second baffle means carried by the lower end cap.

13. The combination of claim 12 wherein the duct is carried by the lower end cap, and the filter is carried by the top cap.

14. The combination of claim 12 wherein said caps are received respectively on opposite ends of the container to insert said duct, said first and second baffle means and filter into the container.

15. The combination of claim 12 wherein the duct extends generally vertically in the container toward the second baffle means, and has a side outlet proximate the second baffle means.

16. The combination of claim 12 wherein the second baffle means includes a primary baffle extending transversely of the container and forming at least one through opening to pass air upwardly from below the primary baffle to the upper side thereof, the primary baffle carried by the duct.

17. The combination claim 16 wherein the second baffle means also includes a secondary baffle that extends about and is spaced from the duct to intercept fluid mucus passing from within the duct to the duct exterior, via said side outlet.

18. The combination of claim 12 including a first tube attached to the top cap and extending downwardly into the container, the first baffle means carried by the first tube in series with said opening in the top cap.

19. The container of claim 18 wherein the first baffle means includes a second tube attached to the top cap and extending downwardly into the container, about the first tube and spaced therefrom, to pass suction air to the filter in the first tube.

20. The combination of claim 12 wherein the first baffle means also includes a transverse baffle carried by the second tube to extend transversely within the container below the first tube, the transverse baffle forming at least one suction air passing through opening to pass suction air upwardly to the exterior of the second tube which in turn receives such air to flow downwardly therein, whereby counterflow of suction air is established to remove mucus therefrom in response to air flow direction reversal.

21. The device of claim 12 including external, flexible tubing extending downwardly from said lower end cap and terminating at a catheter, and a catheter support on the lower end cap.

* * * * *